US012635949B2

(12) United States Patent
Ghannad-Rezaie et al.

(10) Patent No.: US 12,635,949 B2
(45) Date of Patent: May 26, 2026

(54) MONITORING FIT OF WEARABLE DEVICES

(71) Applicant: Whoop, Inc., Boston, MA (US)

(72) Inventors: Mostafa Ghannad-Rezaie, Malden, MA (US); Behnoosh Tavakoli, Needham, MA (US)

(73) Assignee: Whoop, Inc., Boston, MA (US)

( * ) Notice: Subject to any disclaimer, the term of this patent is extended or adjusted under 35 U.S.C. 154(b) by 766 days.

(21) Appl. No.: 17/939,722

(22) Filed: Sep. 7, 2022

(65) Prior Publication Data

US 2023/0070753 A1      Mar. 9, 2023

Related U.S. Application Data

(60) Provisional application No. 63/241,438, filed on Sep. 7, 2021.

(51) Int. Cl.
A61B 5/00 (2006.01)
A61B 5/024 (2006.01)

(52) U.S. Cl.
CPC ........ A61B 5/6843 (2013.01); A61B 5/02438 (2013.01); A61B 5/6804 (2013.01); A61B 5/6831 (2013.01); A61B 5/742 (2013.01); A61B 5/7455 (2013.01)

(58) Field of Classification Search
CPC . A61B 5/6843; A61B 5/02438; A61B 5/6804; A61B 5/6831; A61B 5/742; A61B 5/7455; A61B 5/681
USPC ...................................................... 340/407.1
See application file for complete search history.

(56) References Cited

U.S. PATENT DOCUMENTS

| 11,347,320 | B1 | 5/2022 | Shin |
| 2002/0124295 | A1 | 9/2002 | Fenwick et al. |
| 2010/0292599 | A1 | 11/2010 | Oleson et al. |
| 2014/0180019 | A1 | 6/2014 | Martinez et al. |

(Continued)

FOREIGN PATENT DOCUMENTS

| EP | 3332698 | 6/2018 |
| WO | WO-2009147615 | 12/2009 |

(Continued)

OTHER PUBLICATIONS

ISA/EP, "PCT Application No. PCT/US22/42774 International Search Report and Written Opinion mailed Jan. 22, 2022", 11 pages.

(Continued)

*Primary Examiner* — Omar CasillasHernandez
(74) *Attorney, Agent, or Firm* — Strategic Patents, P.C.

(57) ABSTRACT

Tightness of a wearable device can be evaluated through direct observations of how the device responds to a physical stimulus. For example, by applying a varying pattern of vibrations such as a CHIRP signal with a haptic output element or the like to a device strapped to a wrist or other body part, the mechanical and/or optical response of the device can be measured to infer the amount of tension that is retaining the device against the body, or more generally, to evaluate whether the device is properly fitted to a user. Results can then be presented to a user objectively using Newtons or some other metric, or subjectively by providing qualitative assessments of fit. Recommendations for adjustments may also or instead be provided to the user for optimal performance of the wearable device.

20 Claims, 10 Drawing Sheets

(56)     References Cited

U.S. PATENT DOCUMENTS

| | | | |
|---|---|---|---|
| 2016/0135743 A1 | 5/2016 | Cobbett et al. | |
| 2016/0266606 A1 | 9/2016 | Ricci | |
| 2017/0086742 A1* | 3/2017 | Harrison-Noonan | A61B 5/6843 |
| 2018/0204426 A1* | 7/2018 | Nagisetty | H04B 1/385 |
| 2018/0220962 A1 | 8/2018 | Palley et al. | |
| 2018/0242654 A1 | 8/2018 | Marikkar et al. | |
| 2018/0338686 A1* | 11/2018 | Tokita | A61B 5/6844 |
| 2018/0356888 A1* | 12/2018 | Rihn | G01L 5/103 |
| 2019/0110748 A1 | 4/2019 | Cho et al. | |
| 2019/0142341 A1 | 5/2019 | Harrison-noonan et al. | |
| 2019/0159680 A1 | 5/2019 | Tanaka et al. | |
| 2021/0132695 A1* | 5/2021 | Yokoyama | G06F 3/016 |
| 2021/0401314 A1 | 12/2021 | Pho et al. | |
| 2021/0401378 A1 | 12/2021 | Pho et al. | |
| 2021/0407684 A1 | 12/2021 | Pho et al. | |
| 2022/0409187 A1 | 12/2022 | Pho et al. | |

FOREIGN PATENT DOCUMENTS

| | | |
|---|---|---|
| WO | WO-2014188171 | 11/2014 |
| WO | WO-2015134654 | 9/2015 |
| WO | WO-2016123129 | 8/2016 |
| WO | WO-2019168475 | 9/2019 |
| WO | WO-2019213114 | 11/2019 |
| WO | WO-2023038983 | 3/2023 |

OTHER PUBLICATIONS

Smarr, Benjamin L. et al., "Feasibility of continuous fever monitoring using wearable devices", Scientific Reports | (2020) 10:21640, https://doi.org/10.1038/s41598-020-78355-6 NPL-333 Dec. 14, 2020 , 11 Pages.

WIPO, "PCT Application No. PCT/US22/42774 International Preliminary Report on Patentability mailed Mar. 21, 2024", 8 pages.

IPO, , "IN Application No. 202417021602 First Examination Report mailed Mar. 12, 2026", , 7 pages.

* cited by examiner

400

| COUPLE MONITOR TO BODY 402 | → | STORE MODEL 404 | → | VIBRATE MONITOR 406 | → | MEASURE RESPONSE 408 | → | CALCULATE TENSION 410 | → | PROVIDE ADJUSTMENT INFORMATION 412 |

500

VIBRATE MONITOR
502

MEASURE RESPONSE
504

CALCULATE MECHANICAL COUPLING
506

CALCULATE OPTICAL COUPLING
508

EVALUATE FIT
510

PROVIDE ADJUSTMENT INFORMATION
512

800

MONITORING FIT OF WEARABLE DEVICES

CROSS-REFERENCE TO RELATED APPLICATIONS

This application claims priority to U.S. Provisional Application No. 63/241,438 filed on Sep. 7, 2021, the entire content of which is hereby incorporated by reference.

BACKGROUND

Improper fit can be a major source of inconsistency for data acquisition from wearable physiological monitors that use optical sensing, capacitive sensing, or other contact-based sensing techniques. For example, when an optical monitoring system, such as a photoplethysmography monitor or blood oxygenation monitor, is too loose, the signal can deteriorate due to poor optical coupling between the sensor and the skin. Conversely, when a monitor is too tight, the monitor may constrain blood circulation under the sensor and reduce the quality or strength of the optical signal. Fortunately, there may be a range of optimal normal forces for such sensors that can securely retain the sensors in contact with the skin without impairing signal acquisition or data accuracy, even during periods of intense activity and motion. However, a user will typically adjust tightness based on a subjective feeling of comfort or fashion, rather than optimal device performance.

There remains a need for techniques to monitor the fit of wearable physiological monitors, e.g., in order to provide objective user feedback on the proper tension for good device performance.

SUMMARY

Tightness of a wearable device can be evaluated through direct observations of how the device responds to a physical stimulus. For example, by applying a varying pattern of vibrations such as a CHIRP signal with a haptic output element or the like to a device strapped to a wrist or other body part, the mechanical and/or optical response of the device can be measured to infer the amount of tension that is retaining the device against the body, or more generally, to evaluate whether the device is properly fitted to a user. Results can then be presented to a user objectively using Newtons or some other metric, or subjectively by providing qualitative assessments of fit. Recommendations for adjustments may also or instead be provided to the user for optimal performance of the wearable device.

In an aspect, a computer program product disclosed herein may include computer executable code embodied in a non-transitory computer readable medium that, when executing on one or more computing devices, performs the steps of: causing a vibration of a wearable heart rate monitor coupled to a body of a user with an elastic strap by activating a haptic output element on the wearable heart rate monitor; measuring a response of the wearable heart rate monitor to the vibration; calculating a tension of a strap of the wearable heart rate monitor about the body by applying a physical model for the wearable heart rate monitor and the elastic strap to the response to the vibration; and providing adjustment information to the user based on the tension indicating whether the tension is within an acceptable range. The physical model may be a resonance model.

In an aspect, a method disclosed herein may include: causing a vibration of a wearable monitor coupled to a body of a user; measuring a response of the wearable monitor to the vibration; evaluating a fit of the wearable monitor to the body based on the response; and providing adjustment information to the user to adjust the fit to a predetermined target.

Implementations may include one or more of the following features. The predetermined target may include a tension in a band securing the wearable monitor to the user. The predetermined target may include a normal force of the wearable monitor against a skin of the user. The response may include an optical response from one or more optical sensors and a mechanical response from one or more motion sensors, where the method may further include: calculating a level of optical coupling of the wearable monitor to the user with a first signal from the one or more optical sensors; calculating a level of mechanical coupling of the wearable monitor to the user with a second signal from the one or more motion sensors; and evaluating the fit based on a combination of the level of optical coupling and the level of mechanical coupling. Causing the vibration may include activating a haptic output element coupled to the wearable monitor. Evaluating the fit may include calculating a level of mechanical coupling with a processor on the wearable monitor. Providing adjustment information to the user may include presenting the adjustment information in a user interface of a computing device associated with the user. The adjustment information may indicate a level of tightness of the wearable monitor. The adjustment information may include an instruction for adjusting the wearable monitor about the body. Measuring the response may include receiving motion data during the vibration from one or more accelerometers. Measuring the response may include receiving motion data during the vibration from one or more gyroscopes. Measuring the response may include receiving optical data during the vibration from one or more light detectors. Causing the vibration may include activating a linear haptic output element. The wearable monitor may be coupled to a wrist of the user with a wristband. The wearable monitor may be coupled to the body with an elastic article of clothing.

In an aspect, a system disclosed herein may include: a wearable monitor including a processor, at least one sensor, and a haptic output element; computer executable code stored in a memory of the wearable monitor that configures the processor to cause a vibration of the haptic output element and receive a response to the vibration from the at least one sensor; and a remote processing resource coupled in a communicating relationship with the wearable monitor, the remote processing resource including a second memory storing a physical model of the wearable monitor and a second processor configured to receive the response to the vibration from the wearable monitor, to calculate a level of mechanical coupling of the wearable monitor about a body of a user based on the response, to calculate a level of optical coupling of the wearable monitor about the body independently from the level of mechanical coupling based on the response, to evaluate a fit of the wearable monitor to the user based on the level of optical coupling and the level of mechanical coupling, and to communicate adjustment information to the user based on a different between the fit and a predetermined target fit for the wearable monitor. The predetermined target fit may include at least one of a minimum tension, a maximum tension, and a range of tensions. The predetermined target fit may include at least one of a minimum threshold, a maximum threshold, and a range.

BRIEF DESCRIPTION OF THE DRAWINGS

The foregoing and other objects, features, and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein. In the drawings, like reference numerals generally identify corresponding elements.

DETAILED DESCRIPTION

Figure 1:
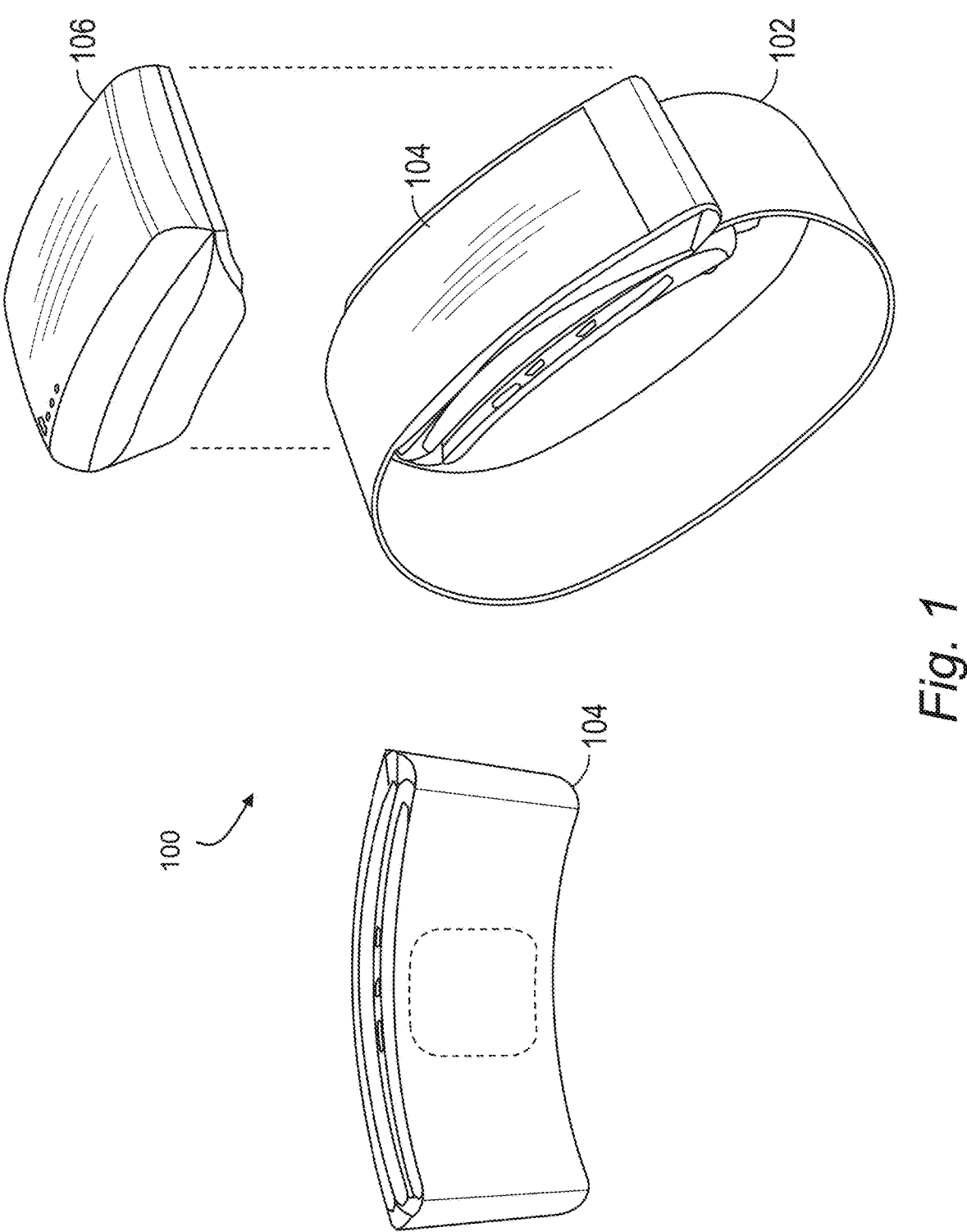
FIG. 1 shows a device for wearable physiological monitoring.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments. Where ranges of values are provided, they are also intended to include each value within the range as if set forth individually, unless expressly stated to the contrary. The use of any and all examples, or exemplary language ("e.g.," "such as," or the like) provided herein, is intended merely to better describe the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," "above," "below," and the like, are words of convenience and are not to be construed as limiting terms unless specifically stated to the contrary.

Exemplary embodiments provide physiological measurement systems, devices and methods for continuous health and fitness monitoring, and provide improvements to overcome the drawbacks of conventional heart rate monitors. One aspect of the present disclosure is directed to providing a lightweight wearable system with a strap that collects various physiological data or signals from a wearer. The strap may be used to position the system on an appendage or extremity of a user, for example, wrist, ankle, and the like. Exemplary systems are wearable and enable real-time and continuous monitoring of heart rate without the need for a chest strap or other bulky equipment which could otherwise cause discomfort and prevent continuous wearing and use. The system may determine the user's heart rate without the use of electrocardiography and without the need for a chest strap. Exemplary systems can thereby be used in not only assessing general well-being but also in continuous monitoring of fitness. Exemplary systems also enable monitoring of one or more physiological parameters in addition to heart rate including, but not limited to, body temperature, heart rate variability, motion, sleep, stress, fitness level, recovery level, effect of a workout routine on health and fitness, caloric expenditure, and the like.

A health or fitness monitor that includes bulky components may hinder continuous wear. Existing fitness monitors often include the functionality of a watch, thereby making the health or fitness monitor quite bulky and inconvenient for continuous wear. Accordingly, one aspect is directed to providing a wearable health or fitness system that does not include bulky components, thereby making the bracelet slimmer, unobtrusive and appropriate for continuous wear. The ability to continuously wear the bracelet further allows continuous collection of physiological data, as well as continuous and more reliable health or fitness monitoring. For example, embodiments of the bracelet disclosed herein allow users to monitor data at all times, not just during a fitness session. In some embodiments, the wearable system may or may not include a display screen for displaying heart rate and other information. In other embodiments, the wearable system may include one or more light emitting diodes (LEDs) to provide feedback to a user and display heart rate selectively. In some embodiments, the wearable system may include a removable or releasable modular head that may provide additional features and may display additional information. Such a modular head can be releasably installed on the wearable system when additional information display is desired and removed to improve the comfort and appearance of the wearable system. In other embodiments, the head may be integrally formed in the wearable system.

Exemplary embodiments also include methods for measuring tightness of a wearable monitor and providing actionable feedback to a user. The tightness of the wearable monitor may have an impact on its performance. To help ensure a good fit, a physical model such as a spring model or resonance model may be created to characterize movement of the wearable monitor when elastically retained in tension about a body part. The wearable monitor may then be vibrated, and a response to these vibrations may be applied to the model to infer the tension. The inferred tension may be used to provide adjustment information to the user.

The term "continuous," as used herein in connection with heart rate data collection, refers to collection of heart rate data at a sufficient frequency to enable detection of individual heartbeats, and also refers to collection of heart rate data continuously throughout the day and night. More generally with respect to physiological signals that might be monitored by a wearable device, "continuous" or "continuously" will be understood to mean continuously at a rate suitable for intended time-based processing, and physically at a rate possible by the monitoring hardware, subject to ordinary data acquisition limitations such as sampling limitations and sampling rates associated with converting physical signals into digital data, and physical limitations associated with physical disruptions during use, e.g., temporary displacement of monitoring hardware due to sudden movements, changes in external lighting, loss of electrical power, physical manipulation or adjustment by a wearer, physical displacement of monitoring hardware due to external forces, and so forth. It will also be noted that heart rate data or a monitored heart rate, in this context, may more generally refer to raw sensor data, heart rate data, signal peak data, heart rate variability data, or any other physiological or digital signal suitable for recovering heart rate data as contemplated herein, and that heart rate data may generally be captured over some historical period that can be subsequently correlated to various metrics such as sleep states, activity recognition, resting heart rate, maximum heart rate, and so forth.

The term "pointing device," as used herein, refers to any suitable input interface, specifically, a human interface device, that allows a user to input spatial data to a computing system or device. In an exemplary embodiment, the pointing device may allow a user to provide input to the computer using physical gestures, for example, pointing, clicking, dragging, and dropping. Exemplary pointing devices may include, but are not limited to, a mouse, a touchpad, a touchscreen, and the like.

The term "computer-readable medium," as used herein, refers to a non-transitory storage hardware, non-transitory storage device or non-transitory computer system memory that may be accessed by a controller, a microcontroller, a computational system or a module of a computational system to encode thereon computer-executable instructions or software programs. The "computer-readable medium" may be accessed by a computational system or a module of a computational system to retrieve and/or execute the computer-executable instructions or software programs encoded on the medium. The non-transitory computer-readable media may include, but are not limited to, one or more types of hardware memory, non-transitory tangible media (for example, one or more magnetic storage disks, one or more optical disks, one or more USB flash drives), computer system memory or random access memory (such as, DRAM, SRAM, EDO RAM) and the like.

The term "distal," as used herein, refers to a portion, end or component of a physiological measurement system that is farthest from a user's body when worn by the user.

The term "proximal," as used herein, refers to a portion, end or component of a physiological measurement system that is closest to a user's body when worn by the user.

The term "equal," as used herein, refers, in a broad lay sense, to exact equality or approximate equality within some tolerance.

Exemplary embodiments provide wearable physiological measurements systems that are configured to provide continuous measurement of physiological data such as heart rate or other physiological data such as blood pressure, hydration state, blood oxygenation state, etc. Exemplary systems are configured to be continuously wearable on an appendage, for example, wrist or ankle, and do not rely on electrocardiography or chest straps in detection of heart rate. The exemplary system includes one or more light emitters for emitting light at one or more desired frequencies toward the user's skin, and one or more light detectors for received light reflected from the user's skin. The light detectors may include a photoresistor, a phototransistor, a photodiode, and the like. As light from the light emitters (for example, green light) pierces through the skin of the user, the blood's natural absorbance or transmittance for the light provides fluctuations in the photo-resistor readouts. These waves have the same frequency as the user's pulse since increased absorbance or transmittance occurs only when the blood flow has increased after a heartbeat. The system includes a processing module implemented in software, hardware or a combination thereof for processing the optical data received at the light detectors and continuously determining the heart rate based on the optical data. The optical data may be combined with data from one or more motion sensors, e.g., accelerometers and/or gyroscopes, to minimize or eliminate noise in the heart rate signal caused by motion or other artifacts (or with other optical data of another wavelength).

FIG. 1 shows a physiological monitoring device. The overall system 100 may include a device 104 (which may or may not include a display screen or other user interface) generally configured for physiological monitoring. The system 100 may further include a removable and replaceable battery 106 for recharging the device 104. A strap 102 may be provided, and may include any arrangement suitable for retaining the device 104 in a position on a wearer's body for acquisition of physiological data as described herein. For example, the strap 102 may include slim elastic band formed of any suitable elastic material, for example, a rubber, a woven polymer fiber such as a woven polyester, polypropylene, nylon, spandex, and so forth. The strap 102 may be adjustable to accommodate different wrist sizes, and may include any latches, hasps, or the like to secure the device 104 in an intended position for monitoring a physiological signal. While a wrist-worn device is depicted, it will be understood that the device 104 may be configured for positioning in any suitable location on a user's body, based on the sensing modality and the nature of the signal to be acquired. For example, the device 104 may be configured for use on a wrist, an ankle, a bicep, a chest, or any other suitable location(s), and the strap 102 may be, or may include, a waistband or other elastic band or the like within an article of clothing or accessory. The device 104 may also or instead be structurally configured for placement on or within a garment, e.g., permanently or in a removable and replaceable manner. To that end, the device 104 may be structurally configured for placement within a pocket, slot, and/or other housing that is coupled to or embedded within a garment. In such configurations, the garment may include sensing windows or other pathways such that the device 104 can sense physiological and/or biomechanical parameters from a user wearing a garment that includes the device 104 therein or thereon.

The system 100 may include any hardware components, subsystems, and the like to provide various functions such as data collection, processing, display, and communications with external resources. For example, the system 100 may include a heart rate monitor using, e.g., photoplethysmography, electrocardiography, or any other technique(s). The system 100 may be configured such that, when placed for use about a wrist, the system 100 initiates acquisition of physiological data from the wearer. In some embodiments, the pulse or heart rate may be taken using an optical sensor coupled with one or more light emitting diodes (LEDs), all directly in contact with the user's wrist. The LEDs may be positioned to direct illumination toward the user's skin, and may be accompanied by one or more photodiodes or other photodetectors suitable for measuring illumination from the LEDs that is reflected and/or transmitted by the wearer's skin.

The system 100 may be configured to record other physiological and/or biomechanical parameters including, but not limited to, skin temperature (using a thermometer), galvanic skin response (using a galvanic skin response sensor), motion (using one or more multi-axes accelerometers and/or gyroscope), blood pressure, and the like, as well environmental or contextual parameters such as ambient light, ambient temperature, humidity, time of day, and the like. The system 100 may also include other sensors such as accelerometers and/or gyroscopes for motion detection, and sensors for environmental temperature sensing, electrodermal activity (EDA) sensing, galvanic skin response (GSR) sensing, and the like.

The system 100 may include one or more sources of battery life, such as a first battery environmentally sealed within the device 104 and a battery 106 that is removable and replaceable to recharge the battery in the device 104. The system 100 may perform numerous functions related to continuous monitoring, such as automatically detecting when the user is asleep, awake, exercising, and so forth, and such detections may be performed locally at the device 104 or at a remote service coupled in a communicating relationship with the device 104 and receiving data therefrom. In general, the system 100 may support continuous, independent monitoring of a physiological signal such as a heart rate, and acquired data may be stored on the device 104 until it can be uploaded to a remote processing resource for more computationally expensive analysis.

Figure 2:
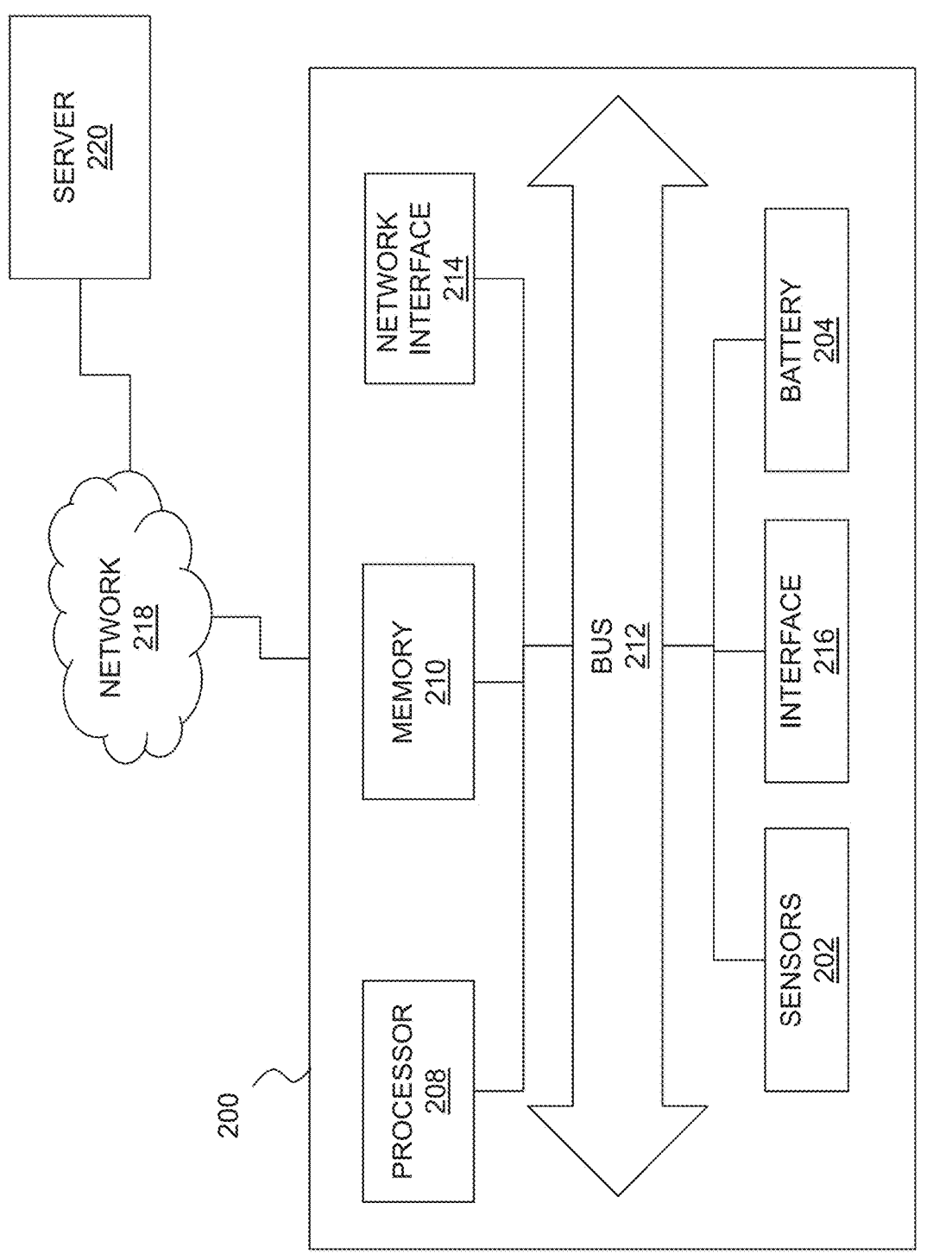
FIG. 2 is a block diagram of a computing device that may be used herein.

FIG. 2 is a block diagram of an exemplary computing device 200 that may be used in to perform any of the methods provided by exemplary embodiments. The computing device may, for example, be a device used for continuous physiological monitoring. The device may also or instead be any of the local computing devices described herein, such as a desktop computer, laptop computer, smart phone. The device may also or instead be any of the remote computing resources described herein, such as a web server, a cloud database, a file server, an application server, or any other remote resource or the like. While described as a physical device, it will be understood that the exemplary computing device 200 may also or instead be realized as a virtual computing device such as a virtual machine executing a web server or other remote resource in a cloud computing platform. In general, the device 200 may include one or more sensors 202, a battery 204, storage 206, a processor 208, memory 210, a network interface 214, and a user interface 216, or virtual instances of one or more of the foregoing.

The sensors 202 may include any sensor or combination of sensors suitable for heart rate monitoring as contemplated herein, as well as sensors 202 for detecting calorie burn, position (e.g., through a Global Positioning System or the like), motion, activity and so forth. In one aspect, this may include optical sensing systems including LEDs or other light sources, along with photodiodes or other light sensors, that can be used in combination for photoplethysmography measurements of heart rate, pulse oximetry measurements, and other physiological monitoring.

The sensors 202 may also or instead include one or more sensors for activity measurement. In some embodiments, the system may include one or more multi-axes accelerometers and/or gyroscope to provide a measurement of activity. In some embodiments, the accelerometer may further be used to filter a signal from the optical sensor for measuring heart rate and to provide a more accurate measurement of the heart rate. In some embodiments, the wearable system may include a multi-axis accelerometer to measure motion and calculate distance. Motion sensors may be used, for example, to classify or categorize activity, such as walking, running, performing another sport, standing, sitting or lying down. The sensors 202 may, for example, include a thermometer for monitoring the user's body or skin temperature. In one embodiment, the sensors 202 may be used to recognize sleep based on a temperature drop, Galvanic Skin Response data, lack of movement or activity according to data collected by the accelerometer, reduced heart rate as measured by the heart rate monitor, and so forth. The body temperature, in conjunction with heart rate monitoring and motion, may be used, e.g., to interpret whether a user is sleeping or just resting, as well as how well an individual is sleeping. The body temperature, motion, and other sensed data may also be used to determine whether the user is exercising, and to categorize and/or analyze activities as described in greater detail below. In another aspect, the sensors 202 may include one or more contact sensors, such as a capacitive touch sensor or resistive touch sensor, for detecting placement of a physiological monitor for use on a user. More generally, the sensors 202 may include any sensor or combination of sensors suitable for monitoring geographic location, physiological state, exertion, movement, and so forth in any manner useful for physiological monitoring as contemplated herein.

The battery 204 may include one or more batteries configured to allow continuous wear and usage of the wearable system. In one embodiment, the wearable system may include two or more batteries, such as a removable battery that may be removed and recharged using a charger, along with an integral battery that maintains operation of the device 200 while the main battery charges. In another aspect, the battery 204 may include a wireless rechargeable battery that can be recharged using a short range or long range wireless recharging system.

The processor 208 may include any microprocessor, microcontroller, signal processor or other processor or combination of processors and other processing circuitry suitable for performing the processing steps described herein. In general, the processor 208 may be configured by computer executable code stored in the memory 210 to provide activity recognition and other physiological monitoring functions described herein.

In general the memory 210 may include one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, optical disks, USB flash drives), and the like. In one aspect, the memory 210 may include a computer system memory or random access memory, such as DRAM, SRAM, EDO RAM, and the like. The memory 210 may include other types of memory as well, or combinations thereof, as well as virtual instances of memory, e.g., where the device is a virtual device. In general, the memory 210 may store computer readable and computer-executable instructions or software for implementing methods and systems described herein. The memory 210 may also or instead store physiological data, user data, or other data useful for operation of a physiological monitor or other device described herein, such as data collected by sensors 202 during operation of the device 200.

The network interface 214 may be configured to wirelessly communicate data to a server 220, e.g., through an external network 218 such as any public network, private network, or other data network described herein, or any combination of the foregoing including, e.g., local area networks, the Internet, cellular data networks, and so forth. Where the device is a physiological monitoring device, the network interface 214 may be used, e.g., to transmit raw or processed sensor data stored on the device 200 to the server 220, as well as to receive updates, receive configuration information, and otherwise communicate with remote resources and the user to support operation of the device. More generally, the network interface 214 may include any interface configured to connect with one or more networks, for example, a Local Area Network (LAN), a Wide Area Network (WAN), the Internet, or a cellular data network through a variety of connections including, but not limited to, standard telephone lines, LAN or WAN links (for example, 202.11, T1, T3, 56 kb, X.25), broadband connections (for example, ISDN, Frame Relay, ATM), wireless connections, or some combination of any or all of the above. The network interface 212 may include a built-in network adapter, network interface card, PCMCIA network card, card bus network adapter, wireless network adapter, USB network adapter, modem or any other device suitable for interfacing the computing device 200 to any type of network capable of communication and performing the operations described herein.

The user interface 216 may include any components suitable for supporting interaction with a user. This may, for example include a keypad, display, buzzer, speaker, light emitting diodes, and any other components for receiving input from, or providing output to, a user. In one aspect, the device 200 may be configured to receive tactile input, such as by responding to sequences of taps on a surface of the device to change operating states, display information and so forth. The user interface 216 may also or instead include a graphical user interface rendered on a display for graphical user interaction with programs executing on the processor 208 and other content rendered by a physical display of device 200.

Figure 3:
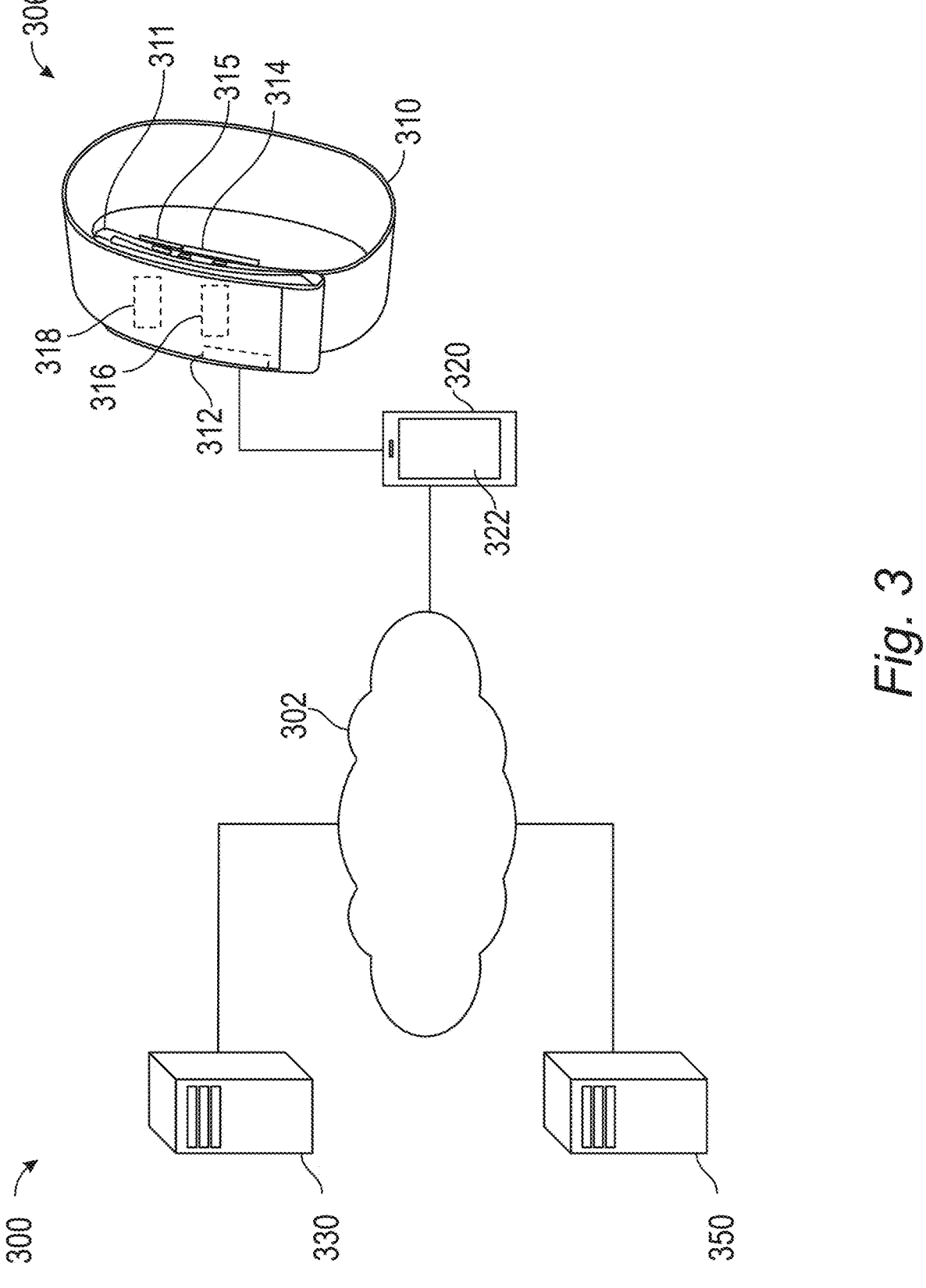
FIG. 3 illustrates a physiological monitoring system.

FIG. 3 illustrates a physiological monitoring system. More specifically, FIG. 3 illustrates a system 300 facilitating physiological monitoring that may be used with any of the methods or devices described herein. In general, the system 300 may include a physiological monitor 306, a user device

320, a remote server 330 with a remote data processing resource (such as any of the processors or processing resources described herein), and one or more other resources 350, all of which may be interconnected through a data network 302.

The data network 302 may be any of the data networks described herein. For example, the data network 302 may be any network(s) or internetwork(s) suitable for communicating data and information among participants in the system 300. This may include public networks such as the Internet, private networks, telecommunications networks such as the Public Switched Telephone Network or cellular networks using third generation (e.g., 3G or IMT-2000), fourth generation (e.g., LTE (E-UTRA) or WiMAX-Advanced (IEEE 802.16m)), fifth generation (e.g., 5G), and/or other technologies, as well as any of a variety of corporate area or local area networks and other switches, routers, hubs, gateways, and the like that might be used to carry data among participants in the system 300. This may also include local or short range communications networks suitable, e.g., for coupling the physiological monitor 306 to the user device 320, or otherwise communicating with local resources.

The physiological monitor 306 may, in general, be any physiological monitoring device, such as any of the wearable monitors or other monitoring devices described herein, such as bracelet 100 in FIG. 1. Thus, the physiological monitor 306 may generally be shaped and sized to be worn on a wrist or other appendage of a user and retained in a desired orientation relative to the appendage with a strap 310 or other attachment mechanism. The physiological monitor 306 may include a wearable housing 311, a network interface 312, one or more sensors 314, one or more light sources 315, a processor 316, a memory 318, and a wearable strap 310 for retaining the physiological monitor 306 in a desired location on a user.

In general, the physiological monitor 306 may include a wearable physiological monitor configured to acquire heart rate data and/or other physiological data from a wearer. More specifically, the wearable housing 311 of the physiological monitor 306 may be configured such that a user can wear a wearable physiological monitor 306 to acquire heart rate data and/or other physiological data from the user in a substantially continuous manner. The wearable housing 311 may be configured for cooperation with a strap 310 or the like, e.g., for engagement with an appendage of a user.

The network interface 312 may be configured to coupled one or more participants of the system 300 in a communicating relationship, e.g., with the remote server 330. The network interface 312 may be configured to couple one or more participants of the system 300 in a communicating relationship, e.g., with the remote resource using techniques such as Bluetooth, Wi-Fi (Wireless-Fidelity), the mobile network (3G, 4G, 5G, . . . ), or near field communication (NFC).

The one or more sensors 314 may include any of the sensors described herein, or any other sensors suitable for physiological monitoring. By way of example and not limitation, the one or more sensors 314 may include one or more of a light source, and optical sensor, an accelerometer, a gyroscope, a temperature sensor, a galvanic skin response sensor, an environmental sensor (e.g., for measuring ambient temperature, humidity, lighting, and the like), a geolocation sensor, a temporal sensor, an electrodermal activity sensor, and the like. The one or more sensors 314 may be disposed in the wearable housing 311, or otherwise positioned and configured for capture of data for physiological monitoring of a user. In one aspect, the one or more sensors 314 may include a light detector configured to provide data to the processor 316 for calculating a heart rate variability. The one or more sensors 314 may also or instead include an accelerometer configured to provide data to the processor 316, e.g., for detecting a sleep state, a waking event, exercise, and/or other user activity. In an implementation, the one or more sensors 314 may measure a galvanic skin response of the user.

The processor 316 and memory 318 may be any of the processors and memories described herein, and may be suitable for deployment in a physiological monitoring device. In one aspect, the memory 318 may store physiological data obtained by monitoring a user with the one or more sensors 314. The processor 316 may be configured to obtain heart rate data from the user based on the data from the sensors 314. The processor 316 may be further configured to assist in a determination of a condition of the user, such as whether the user has an infection or other condition of interest as described herein.

The one or more light sources 315 may be coupled to the wearable housing 311 and controlled by the processor 316. At least one of the light sources 315 may be directed toward the skin of a user's appendage. Light from the light source 315 may be detected by the one or more sensors 314.

The system 300 may further include a remote data processing resource executing on a remote server 330. The remote data processing resource may be any of the processors described herein, and may be configured to receive data transmitted from the memory 318 of the physiological monitor 306, and to evaluate a condition of the user such as whether the user has an infection or other condition of interest as described herein.

The system 300 may also include one or more user devices 320, which may work together with the physiological monitor 306, e.g., to provide a display for user data and analysis, and/or to provide a communications bridge from the network interface 312 of the physiological monitor 306 to the data network 302 and the remote server 330. For example, the physiological monitor 306 may communicate locally with the user device 320, such as a smartphone of a user, via short-range communications, e.g., Bluetooth, or the like, e.g., for the exchange of data between the physiological monitor 306 and the user device 320, and the user device 320 may communicate with the remote server 330 via the data network 302. Computationally intensive processing may be performed at the remote server 330, which may have greater memory capabilities and processing power than the physiological monitor 306 that acquires the data. However, it will be understood that processing may also or instead be performed at one or more of the physiological monitor 306, the user device 320, and so on. That is, it will be understood that one or more of the steps related to techniques for physiological monitoring as described herein, or sub-steps, calculations, functions, and the like related thereto, can be performed locally, remotely, or some combination of these. For example, these steps may be performed locally on a wearable device, remotely on a server or other remote resource, on an intermediate device such as a local computer used by the user to access the remote resource, or any combination of these.

The user device 320 may include any computing device as described herein, including without limitation a smartphone, a desktop computer, a laptop computer, a network computer, a tablet, a mobile device, a portable digital assistant, a cellular phone, a portable media or entertainment device, and so on. The user device 320 may provide a user interface 322 for access to data and analysis by a user, and/or to control operation of the physiological monitor 306. The user interface 322 may be maintained by an application executing locally on the user device 320, or the user interface 322 may be remotely served and presented on the user device 320, e.g., from the remote server 330 or the one or more other resources 350.

In general, the remote server 330 may include data storage, a network interface, and/or other processing circuitry. The remote server 330 may process data from the physiological monitor 306, and the remote server 330 may perform any of the analyses described herein, and may host a user interface for remote access to this data, e.g., from the user device 320. The remote server 330 may include a web server or other programmatic front end that facilitates web-based access by the user devices 320 and/or the physiological monitor 306 to the capabilities of the remote server 330 or other components of the system 300.

The other resources 350 may include any resources that can be usefully employed in the devices, systems, and methods as described herein. For example, these other resources 350 may include without limitation other data networks, human actors (e.g., programmers, researchers, annotators, editors, analysts, and so forth), sensors (e.g., audio or visual sensors), data mining tools, computational tools, data monitoring tools, algorithms, and so forth. The other resources 350 may also or instead include any other software or hardware resources that may be usefully employed in the networked applications as contemplated herein. For example, the other resources 350 may include payment processing servers or platforms used to authorize payment for access, content, or option/feature purchases, or otherwise. In another aspect, the other resources 350 may include certificate servers or other security resources for third-party verification of identity, encryption or decryption of data, and so forth. In another aspect, the other resources 350 may include a desktop computer or the like co-located (e.g., on the same local area network with, or directly coupled to through a serial or USB cable) with a user device 320, physiological monitor 306, and/or remote server 330. In this case, the other resources 350 may provide supplemental functions for other components of the system 300.

The other resources 350 may also or instead include one or more web servers that provide web-based access to and from any of the other participants in the system 300. While depicted as a separate network entity, it will be readily appreciated that the other resources 350 (e.g., a web server) may also or instead be logically and/or physically associated with one of the other devices described herein, and may for example, include or provide a user interface 322 for web access to a remote server 330 or a database in a manner that permits user interaction through the data network 302, e.g., from the physiological monitor 306 and/or the user device 320.

Figure 4:
FIG. 4 is a flow chart illustrating a method for measuring fit of a wearable monitor and providing actionable feedback to a user.
Figure 4:
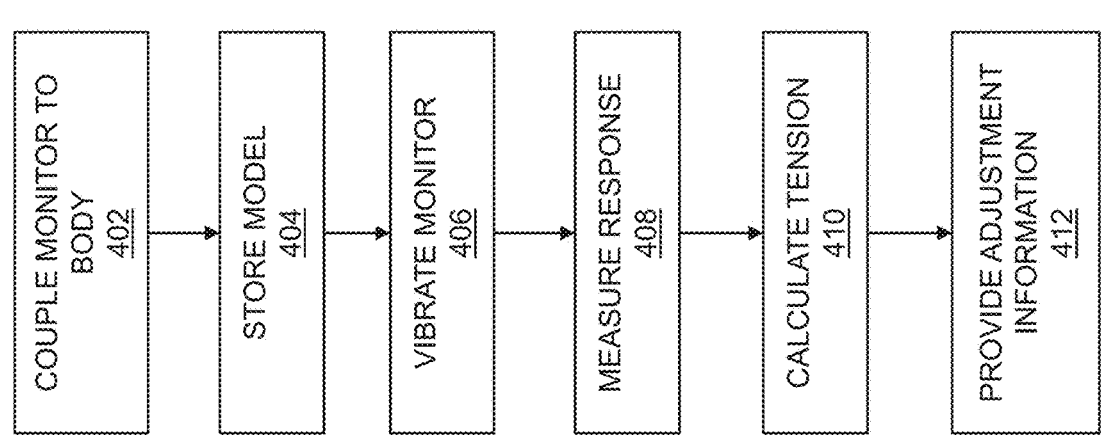

FIG. 4 is a flow chart illustrating a method 400 for measuring tightness of a wearable monitor and providing actionable feedback to a user based on a physical model. The tightness of a wearable monitor can have an impact on performance. For example, when an optical monitor, such as a photoplethysmography monitor or blood oxygenation monitor, is too loose, the resulting signal can deteriorate due to poor optical coupling between the sensor and the skin. To help ensure an optimal level of tightness, a physical model such as a spring model or a resonance model may be created to characterize movement of the wearable monitor when elastically retained in tension about a body part. The wearable monitor may then be vibrated, and a measured response to these vibrations may be used with the physical model to infer the tension, e.g., by calculating a tension for the physical model that yields a response to the vibration equivalent to the measured response. The inferred tension may then be used to provide adjustment information to the user, e.g., to tighten, loosen, reposition, and/or otherwise adjust the monitor for improved or proper operation.

As shown in step 402, the method 400 may include coupling a wearable monitor to a body of a user. The monitor may include a physiological monitor, an optical monitor, a photoplethysmography system, a pulse oxygen monitor, or any of the other wearable physiological monitors described herein, or any other monitor that might be coupled to a body of a user with an elastic strap, band, fabric, elastic clothing, or the like. For example, the monitor may be coupled to a wrist of a user with a wristband. The monitor may instead be coupled to a chest, a bicep, an ankle, a calf, a torso, a waist, a leg, an arm, or some other body part with an elastic strap or an elastic article of clothing formed of an athletic knit such as Lycra, spandex, elastane, one or more elastic straps, or some other fabric or elastic material formed of a polymer, polyurethane rubber, or the like. The monitor may usefully include a haptic output device and motion sensors such as accelerometers, gyroscopes, and/or magnetometers in order to provide a stimulus and response for fit detection as described herein. While the techniques described herein are generally described in the context of wearable physiological monitors, the techniques may more generally be applied to any system where proper performance depends on a tension (or corresponding normal force) with which a device is elastically retained in an intended position, and all such uses are intended to fall within the scope of this disclosure unless expressly stated otherwise.

As shown in step 404, the method 400 may include storing a model for physical behavior of the wearable monitor to motion. This may, for example, include a physical model such as a resonance model characterizing how the wearable monitor and any elastic tensioning members move in response to an applied force, e.g., as a function of tension in one or more elastic tensioning members (or a lumped characterization of same). The model may be any empirical, analytical, or other model suitable for relating a vibration response to a tension in the elastic tensioning members. In one aspect, a resonance model provides a useful approximation that has been demonstrated to yield accurate tension calculations suitable for the purposes contemplated herein. One such resonance model based on a spring system is now discussed in greater detail by way of example. However, the physical model may more generally include any suitable type of system model based on mechanical inputs and resulting motion (or optical response, as further discussed below). The model of physical behavior may also or instead include an empirical or data driven model trained to identify tension based on training data sets of mechanical/optical responses labeled by a suitable training metric such as physical tension, device fit, measurement accuracy, and so forth.

In general, the tightness of the wearable sensor may be characterized as the pressure that the sensor optical interface applies to the skin to maintain contact. Given the total normal force pushing the strap to the skin (F) and the contact area of a sensor (A), assuming the pressure is uniformly distributed, the strap tightness maybe calculated as F/A. The uniform distribution of the pressure over the contract area is a very strong assumption, especially during motion. The force F between the sensor and the skin when the sensor is facing up and when the second facing down may be adjusted according to the forces of gravity as follows:

$$F=\sin(\alpha)2f+mg$$

and $$F=\cos(\alpha)2f-mg$$

respectively, where $\alpha$ is the angle between the strap and the garment, f is the tightness of the garment, m is the weight of the sensor, and g is the gravity coefficient (acceleration due to gravity). When the garment, strap, or other elastic tensioning member is elastic with a spring constant of k:

$$f=k(dx)$$

where dx is the change of the strap length and f is the tightness of the elastic tensioning member. In practice, k is a monotonic function of dx over the elastic range of interest. Given these equations, a direct relationship can be derived between tightness and the force between strap and skin in a stationary state. The force between the skin and the sensor in motion can be calculated given an acceleration vector and the weight of the sensor. This framework generally confirms that physical displacement of the device is a function of strap tension and applied forces, and that if k is known or calculated, the tightness (and consequently the force between the sensor and the skin) can also be calculated based on an acceleration vector and a mass of the device. However, directly calculating tension on this basis requires at least calibration of the mechanical force applied by a stimulus (e.g., a haptic device) in response to a control signal. Thus, a resonance model may also or instead be advantageously employed to infer a spring constant based on resonant response to a frequency sweep or the like.

When a force is placed on a material, the material stretches or compresses in response to the force. The force per unit area is the stress ($\sigma$). The extent of the stretching/compression produced as the material responds to stress is the strain ($\epsilon$). Strain is measured by the ratio of the difference in length $\Delta L$, L to original length $L_0$, along the direction of the stress, i.e., $\epsilon=\Delta L/L_0$.

Resonance describes the phenomenon of increased amplitude that occurs when the frequency of an applied force is equal or close to a natural frequency of the system on which it acts. When an oscillation force is applied at a resonant frequency of a dynamic system, the system will oscillate at a higher amplitude than when the same force is applied at other, non-resonant frequencies. The quality factor relates the maximum or peak energy stored in the circuit (the reactance) to the energy dissipated (the resistance) during each cycle of oscillation meaning that it is a ratio of resonant frequency to bandwidth and the higher the circuit Q, the smaller the bandwidth, $Q=f_r/BW$.

These properties maybe used as described herein to characterize a frequency response of the sensor/elastic combination to a mechanical stimulus such as vibration of a haptic output element. A model based on these properties may be stored in any suitable location, e.g., on a memory of the wearable monitor, on a memory of a personal computing device or the like used to perform tension calculations, or on a remote server that performs the tension calculations and provides actionable feedback to the user through the personal computing device (or any combination of these). In one aspect, the resonance model may include an analytical model characterizing strap tension, e.g., of a wrist worn device, as a function of the resonant frequency of the spring system. Depending on the desired range and accuracy of the calculation, this may be a linear model, an exponential model, a quadratic model, or any other model that physically describes the spring system, and that can be fit to experimental data for the spring system. In another aspect, the resonance model may be an empirical or experimental model correlating, e.g., measured resonance frequencies to measured strap tensions. In another aspect, particularly where the observed response does not yield to simple mathematical models, the experimental data may be modeled as a lookup table or the like where tension can be looked up (or interpolated) based on a measured resonant frequency. The actual resonance may be estimated, e.g., based on the wavelength that maximizes measured accelerometer response to haptic input (e.g., a ratio of accelerometer signal to haptic input signal, each of which may be measured in the frequency domain, e.g., to reduce the effects of phase changes or other artifacts).

As shown in step 406, the method 400 may include vibrating the wearable monitor. The vibration may occur upon user request or automatically during a specified event or time. For example, the device may include a button, such as a physical button on the device, or a button in a user interface of another device, that a wearer can press to check for proper fit of a device. In another example, the device may automatically test for fit in response to detected events, such as detecting that a user has put the device on, or detecting a deterioration in data quality below a predetermined threshold while the device is being worn. Vibrating the wearable monitor may, for example, include causing a vibration of the wearable monitor by activating a haptic output element, piezo element, buzzer, eccentric motor, linear vibration motor or other linear haptic actuator, or other vibrator or the like associated with (e.g., mechanically coupled to and/or within a housing of) the wearable monitor. This may include a rotary haptic element, a linear haptic element, or any other haptic element. While rotary vectors for vibration may complicate individual spring measurements, the location of a resonant response can advantageously be performed without resolving rectilinear components of the haptic output and without calibrating haptic amplitude. The control signal for the vibration may, for example, include a chirp signal that increases or decreases in frequency with the passage of time in order to sweep a range of frequencies to locate a resonant frequency (or range of resonant frequencies) for the wearable monitor and elastic tensioning member(s). It will be understood, however, that other signals are also or instead possible for use herein, such as any signal that covers a sufficiently large frequency range for location of resonance. In one aspect, a signal such as a swept sine or cosine may be employed, for example:

$$y = \sin[2\pi(at+f)t]$$

More generally, any linear-frequency chirp, exponential chirp, hyperbolic chirp, or other function that increases or decreases a signal frequency over time may be used. The frequency sweep may be continued until the earlier of (1) achieving a predetermined confidence level for a resonance detection (or a corresponding tension calculation) or (2) a testing timeout. Thus, for example, if a reliable tension measurement cannot be obtained in one-hundred eight seconds (or some other window of time suitable for one or more complete sweeps of a target frequency range) the test may be terminated and an error message may be provided.

As shown in step 408, the method 400 may include measuring a response of the wearable monitor to the vibration, such as by measuring the response with one or more gyroscopes, accelerometers, optical sensors (e.g., by measuring movement against the skin of the user), or any combination of the foregoing or the like. This data may be processed by the wearable monitor or transmitted to a remote resource such as a personal computing device of the user or a remote server for analysis and determination of the elastic tension or circumferential forces retaining the wearable monitor in place.

As shown in step 410, the method 400 may include calculating a tension for the elastic tensioning member (e.g., clothing, strap, band, or the like) that retains the wearable monitor on the body. In general, this may include locating a resonant frequency of the strap/monitor system in response to the chirp or other stimulus, and using this resonant frequency to calculate the spring constant of the system and infer the radial tension. In general, the resonant frequency will be identified at a frequency corresponding to a maximum amplitude in the accompanying mechanical response. Where an analytical model is derived and employed, the tension (or other suitable metric) may be calculated by inputting the measured resonant frequency into the analytically derived equation to calculate tension. As noted above, the model may also or instead be an experimental or empirical model that correlates resonance to tension based on experimental observations. The experimental model may be embodied, e.g., in a look up table, a linear regression model, or some other model that fits measured resonance data to measured strap tension data in a statistically significant manner. Where a lookup table is used, interpolation (e.g., linear interpolation) may also be used if/as appropriate to evaluate tension for interstitial frequencies between values stored in the lookup table. In the latter case, measuring tightness can be performed by simply stimulating the device with a frequency sweep, locating a peak in resonant response, and then, given this resonant frequency, either looking up the tension in a lookup table, or calculating the tension using the regression model or the like.

A shown in step 412, the method 400 may include providing adjustment information to the user, e.g., using any of the techniques described herein. This may, for example, include a quantitative statement of tension, e.g., a circumferential or normal force determined by the calculation, expressed in Newtons or some other physical units. This may also or instead include a score, e.g., of −10 to 10, with zero being the optimal tension, scores between −5 and 5 being acceptable for accurate data acquisition, and anything outside the range of −10 to 10 unlikely to yield accurate or meaningful data. In another aspect, the adjustment information may include qualitative assessments of whether the current tension is within an acceptable range, such as "too tight" (e.g., corresponding to a score as described above greater than 5), "too loose" (e.g., corresponding to a score less than −5), "okay" (e.g., corresponding to a score between −5 and 5), or "optimal" (e.g., corresponding to a score between −1 and 1), or using any similar range bound natural language descriptions. Where information is available concerning the circumference and/or material of the elastic tensioning member(s), or where the model otherwise provides suitable output or analysis, this may include actionable instructions such as "tighten strap at least one millimeter." In one aspect, the actionable instructions may include a visual component illustrating the instructions. Also or instead, if a strap has a built-in, controllable tensioning system that provides specific feedback (e.g., audio, visual, or tactile feedback), actionable instructions may include specific instructions such as "tighten strap three clicks," or the like. In another aspect, if the strap has a built-in, automatic tension controller, the method 400 may include generating control signals to automatically adjust the tension of the strap toward a predetermined tension target.

The adjustment information may be displayed on the wearable monitor or on a local computing device. In one aspect, the adjustment information may be displayed concurrently with one or more other quantitative or qualitative pieces of information such as current physiological measurements for the user. If the wearable monitor detects a user adjustment to strap tension, the monitor may automatically re-test strap tension and/or update the tension metrics or recommendations.

It will be understood that the tension measurement may usefully be repeated under a variety of conditions. For example, the tension measurement may initially be performed when a wearable monitor is placed on the body. The tension measurement may be repeated on a regular schedule, e.g., as a maintenance function, or under conditions indicating a change in tension such as a deteriorating signal strength or decreasing quality/confidence for a physiological metric such as heart rate. In one aspect, the tension measurement may be repeated continuously for a period of time, e.g., at regular, short intervals, when available information indicates that the device is being worn and the tension is outside an acceptable range. In this case, the tension measurement may be repeated until the tension is determined to be in the acceptable range or until a timeout limit is reached. In the latter case, an error notification may be reported to the user, along with a warning that accurate data is not currently being acquired. The tension measurement, or other evaluation of fit, may also or instead be performed on-demand, based on a predetermined user interaction such as touching a button on a user interface, double tapping the device, or the like.

According to the foregoing, a system described herein includes a wearable monitor and a remote processing resource, which may be a remote server or a personal computing device such as a laptop or smart phone for a user of the wearable monitor. The wearable monitor may include a processor, a sensor, and a haptic output element. Computer executable code stored in a memory of the wearable monitor may configure the processor to cause a vibration of the haptic output element and receive a response to the vibration from the sensor. The remote processing resource may be coupled in a communicating relationship with the wearable monitor, and may include a second memory storing a physical model of the wearable monitor and a second processor configured to receive the response to the vibration from the wearable monitor, to apply the physical model to calculate a tension of the wearable monitor about a body part of a user, and to communicate tension information to the user based on the tension. As described herein, the tension may be reported as a physical measurement, an objective fit score, a human-readable evaluation, an instruction for adjustments, or some combination of these.

Figure 5:
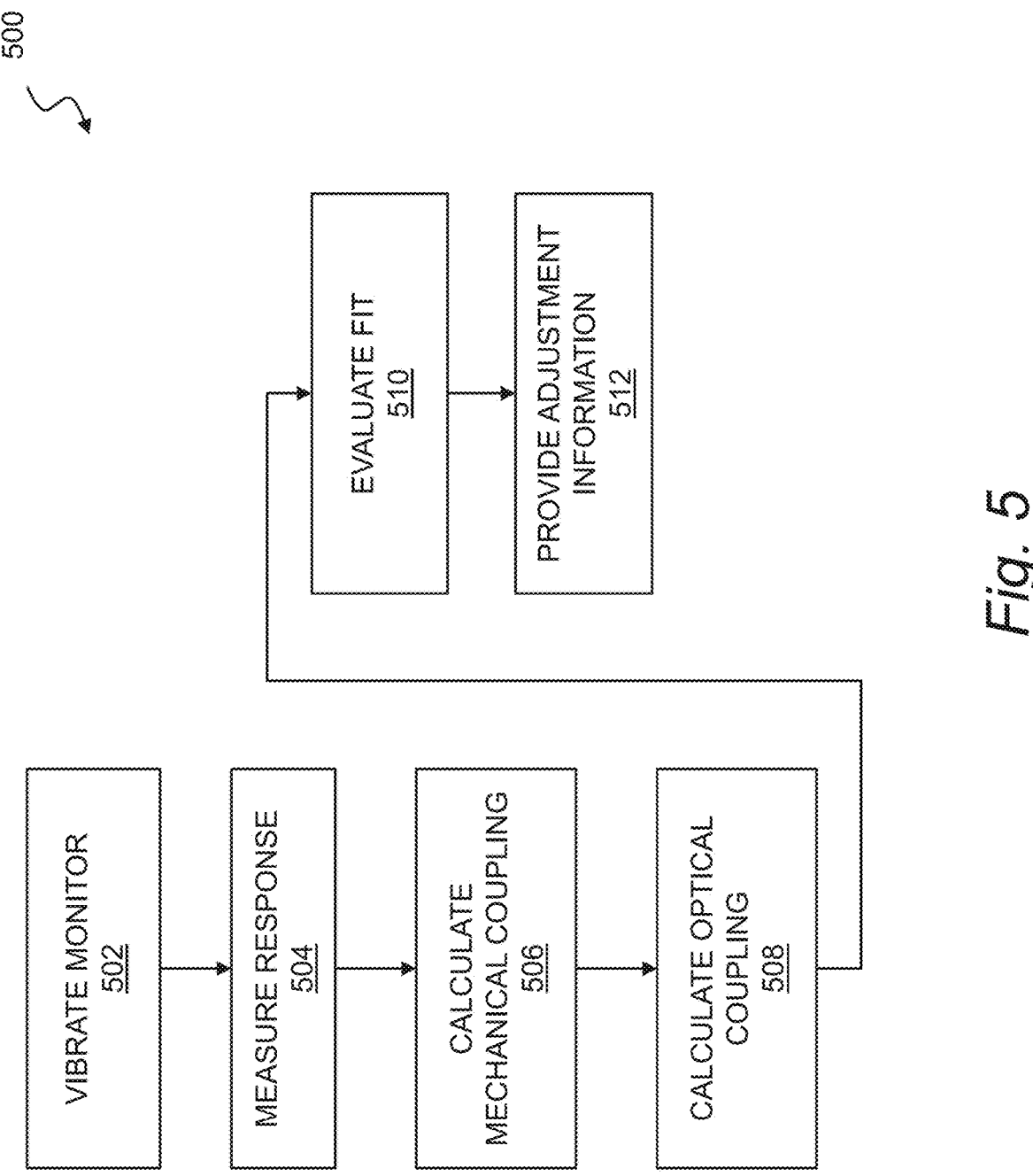
FIG. 5 is a flow chart illustrating a method for measuring fit of a wearable monitor and providing actionable feedback to a user.

FIG. 5 is a flow chart illustrating a method 500 for measuring fit of a wearable monitor. In general, mechanical and optical coupling of the wearable monitor can be measured based on a low resolution haptic stimulus, and used to evaluate fit and provide actionable feedback. As a significant advantage, this approach mitigates the need to calibrate haptic output, or to generate time varying control signals such as frequency sweeps. Instead, the method 500 can be deployed with, e.g., a binary haptic device that is only operable in an 'on' and 'off' mode, and/or that has an unknown and/or varying mechanical orientation relative to the device being tested.

As shown in step 502, the method 500 may include causing a vibration of a wearable monitor coupled to a body of a user. The monitor may include a physiological monitor, an optical monitor, a photoplethysmography system, a pulse oxygen monitor, or any of the other wearable physiological monitors described herein that might be coupled to a body of a user with an elastic strap, band, fabric, or the like. For example, the monitor may be coupled to a wrist of a user with a wristband. The monitor may instead be coupled to a chest, a bicep, an ankle, a calf, a torso, a waist, a leg, an arm, or some other body part with an elastic strap or an elastic article of clothing formed of an athletic knit such as Lycra, spandex, elastane, or some other fabric formed of a polymer, polyurethane rubber, or the like, or any of the other elastic straps or the like described herein. While the techniques described herein are generally described in the context of wearable physiological monitors, the techniques may more generally be applied to any system where proper performance depends on a tension with which a monitor or sensor is elastically retained in an intended position, and all such uses are intended to fall within the scope of this disclosure unless expressly stated otherwise.

The vibration of the wearable monitor may occur upon user request or automatically during a specified event or time, such as when the user puts on the wearable monitor, or more generally at any times and/or using any user interactions described herein. Vibrating the wearable monitor may, for example, include causing a vibration of the wearable monitor by activating a haptic output element such as a piezo element, buzzer, acentric motor, or other vibrator or the like associated with (e.g., mechanically coupled to and/or within a housing of) the wearable monitor. In some embodiments, the haptic output element may be a linear haptic output element configured to deliver haptic outputs along a particular axis. In some embodiments, the vibration may last for one minute or longer.

As shown in step 504, the method 500 may include measuring a response of the wearable monitor to the vibration. For example, measuring the response may include receiving motion data during the vibration, such as data from one or more gyroscopes, accelerometers, or the like, or combinations of the foregoing. Measuring the response may also or instead include receiving optical data during the vibration from one or more light detectors. The response may be processed by the wearable monitor or transmitted to a remote resource such as a personal computing device of the user or a remote server for analysis of the elastic tension or circumferential forces retaining the wearable monitor in place.

As shown in step 506, the method 500 may include calculating a level of mechanical coupling of the wearable monitor about the body based on the response. In general, this includes the coupling between movement along two or more axes. For example, the level of mechanical coupling between a first axis and a second axis may be measured as a phase relationship between a force along the first axis and a force along the second axis. In general, the tighter the wearable monitor is about the body, the smaller the phase relationship (e.g., the closer the response) and thus the larger the mechanical coupling. For a number of axial sensors, the couplings between forces and motions in each axis pair can be inferred from the cross-correlation between measured motion for each axis of that axis pair over time, which in this context, measures the correlation among movements in each axis over time. Thus, for example, a three axis accelerometer system will yield three cross correlations in XY, XZ, and YZ. Similarly, gyroscopic data may yield three cross correlations in rotation for three similar axis pairs. While instantaneous measurements may not provide meaningful results in this context, the average for each axis pair for large numbers of samples will tend to converge on a true cross-correlation for that axis pair where there is actual mechanical coupling between the axes. As such, data may be acquired over an extended interval such as thirty seconds, sixty seconds, ninety seconds, or one hundred eight seconds and/or until a level of confidence in the calculated value(s) meets a predetermined threshold. In this context, the predetermined threshold may be a statistical measure of confidence based on, e.g., a variance in calculated results or mean square error relative to a measurement benchmark.

Figure 6:
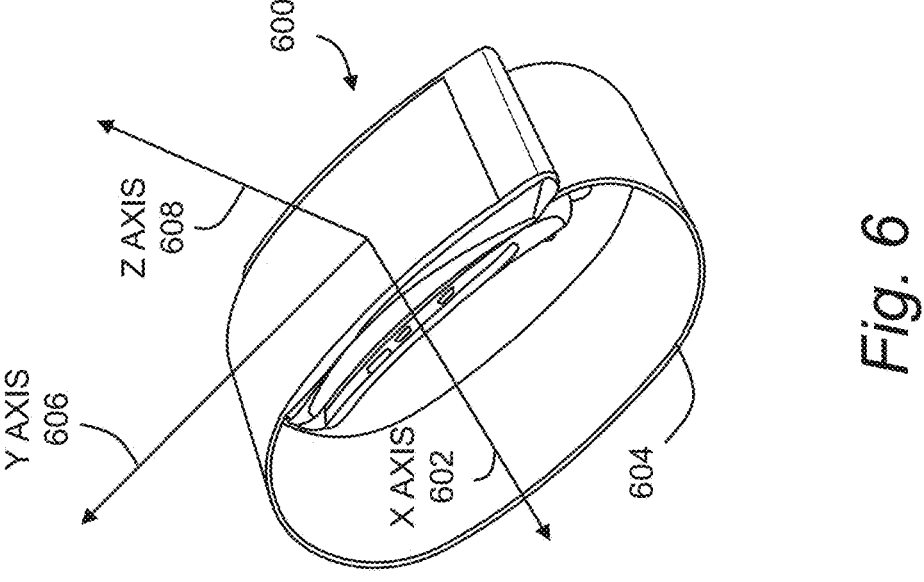
FIG. 6 illustrates a coordinate system for measuring device motion.

While any of the foregoing cross-correlations may be used to measure mechanical coupling as contemplated herein, and each is generally correlated to tightness, there has been observed a monotonic relationship between the ZY mechanical coupling and strap tightness, where the Z axis is normal to the skin, and the Y axis is parallel to the skin and parallel to the strap (as illustrated in FIG. 6 below). This mechanical coupling may be used to estimate strap tension based exclusively on the ZY mechanical coupling. Other couplings between accelerometer and/or gyroscopic axes may also or instead be used, for example, by themselves, in combination with ZY coupling, or as a supplemental or quality control check on inferences based on the ZY coupling.

As shown in step 508, the method 500 may include calculating a level of optical coupling of the wearable monitor about the body based on the response. The level of optical coupling may be calculated independently from the level of mechanical coupling based on the motion data and the optical data. In this case, a similar cross-correlation may be used, however with optical data correlated to acceleration in order to characterize a ratio between two components of the optical signal:heart rate signal (expected to be independent from instantaneous motion) and motion artifacts (expected to be dependent on measured, instantaneous motion). In some embodiments, the motion data may have at least three axes (i.e., from a three-axis IMU, gyroscope, accelerometer, or the like), with X axis data in particular demonstrated as highly correlated to strap tension. As illustrated in FIG. 6 below, the X axis of the device, in this context, is parallel to the skin and perpendicular to the strap.

As shown in step 510, the method 500 may include evaluating fit. This may include scaling, transforming, or otherwise processing the mechanical and optical coupling to obtain a conclusion concerning quantitative tension (e.g., a specific physical measure of tension) or qualitative tension (e.g., a category or human-readable evaluation of tension).

In one aspect, proper fit may be determined by applying ranges and/or thresholds to calculated mechanical and/or optical coupling. In some embodiments, the wearable monitor may be determined to be too tight if the level of mechanical coupling exceeds the threshold and the level of optical coupling is not within the range. In some embodiments, the wearable monitor may be determined to be too loose if the level of mechanical coupling does not exceed the threshold and the level of optical coupling is not within the range. In some embodiments, the wearable monitor may be determined to be at an acceptable tightness level and be coupled to an appendage of the body if the level of mechanical coupling exceeds the threshold and the level of optical coupling is within the range. It will be appreciated that numerical values are relatively arbitrary in this context, and will depend on the manner in which values for mechanical and optical coupling are calculated and reported. However, empirical ranges and thresholds may be readily established for discriminating among properly fitting and improperly fitting devices. It will also be understood that the conditions for proper fit of a strap such as a wrist strap or bicep strap may be different than the conditions for proper fit of a monitor in an article of clothing. Thus, for example, in some embodiments, the wearable monitor may be determined to be at an acceptable tightness level and be coupled to an article of clothing of the user if the level of mechanical coupling does not exceed the threshold and the level of optical coupling is within the range. The threshold and the range may be predetermined values based on the physical properties of wearable monitor, location of the device, physical properties of the tensioning member for the wearable monitor, targets for data quality, and so forth.

In one aspect, fit may be reported as a quantitative statement of tension, e.g., the circumferential or normal force determined by the calculation. In another aspect, the fit may be reported using a quantitative score such as a score on a range of −10 to 10, with zero being the optimal tension, scores between −5 and 5 being acceptable for accurate data acquisition, and anything outside the range of −10 to 10 unlikely to yield accurate or meaningful data. In another aspect, information about the fit may include qualitative assessments of whether the current tension is within an acceptable range, such as "too tight" (e.g., corresponding to a score as described above greater than 5), "too loose" (e.g., corresponding to a score less than −5), "okay" (e.g., corresponding to a score between −5 and 5), or "optimal" (e.g., corresponding to a score between −1 and 1), or using any similar range bound natural language descriptions. The adjustment information may also or instead include actionable instructions such as "tighten strap at least one millimeter," where the physical adjustment estimate is calculated based on the position of the monitor and a corresponding estimate of the body circumference and/or material of the elastic tensioning member(s).

It should also be appreciated that, while various specific techniques are disclosed herein for measuring fit based on response to a haptic vibration or other mechanical stimulus—specifically location of a resonant frequency or measurement of mechanical/optical coupling—other techniques for measuring fit based on the response to haptic vibration may also or instead be used. In one aspect, two or more techniques (such as opto-mechanical coupling and a mathematical model using resonant frequency) may be used concurrently or sequentially, e.g., as a quality control measure or as an alternative where one technique does not yield a useful result.

As shown in step 512, the method 500 may include providing adjustment information, such as by displaying adjustment information to the user based on the level of mechanical coupling and the level of optical coupling. This may include communicating or displaying any of the fit information described herein to the user. In one aspect, this may include actionable instructions including, e.g., verbal or visual instructions concerning an adjustment. Also or instead, if a strap has a built-in, controllable tensioning system that provides specific feedback (e.g., audio, visual, or tactile feedback), actionable instructions may include specific instructions such as "tighten strap three clicks," or similar. In another aspect, if the strap has a built-in, automatic tension controller, providing adjustment information may include generating control signals to automatically adjust the tension of the strap toward a predetermined tension target.

The adjustment information may be displayed on the wearable monitor, on a local computing device, or on any other suitable display device. In one aspect, the adjustment information may be displayed concurrently with one or more quantitative or qualitative pieces of information such as current physiological data for the user. If the wearable monitor detects a user adjustment to strap tension, the monitor may automatically re-test strap tension and/or update tension metrics or recommendations.

Adjustment information may be conditionally provided. For example, providing the adjustment information may be based on a threshold for the level of mechanical coupling and a range for the level of optical coupling. The adjustment information may include a determination of the location of the wearable monitor based on the threshold and the range, which may be reported to the user and/or applied to select a suitable model for evaluating fit as generally described herein.

It will be understood that the tightness measurement may usefully be repeated under a variety of conditions. For example, the tightness measurement may initially be performed when a wearable monitor is placed on the body. The tightness measurement may be repeated on a regular schedule, e.g., as a maintenance function, or under conditions indicating a change in tightness such as a deteriorating signal strength or decreasing quality/confidence for a physiological metric such as heart rate. In one aspect, the tightness measurement may be repeated continuously when adjustment information indicates that the tightness is outside an acceptable range. The tightness measurement may be repeated until the tightness is determined to be in the acceptable range or until a timeout limit has been reached.

According to the foregoing, a system described herein includes a wearable monitor and a remote processing resource, which may be a remote server or a personal computing device such as a laptop or smart phone for a user of the wearable monitor. The wearable monitor may include a processor, a sensor, and a haptic output element. Computer executable code stored in a memory of the wearable monitor may configures the processor to cause a vibration of the haptic output element and receive a response to the vibration from the sensor. The remote processing resource may be coupled in a communicating relationship with the wearable monitor, and may include a second memory storing a physical model of the wearable monitor and a second processor configured to receive the response to the vibration from the wearable monitor, to calculate a level of mechanical coupling of the wearable monitor about a body of a user based on the response, to calculate a level of optical coupling of the wearable monitor about the body independently from the level of mechanical coupling based on the response, and to communicate adjustment information to the user based on the level of mechanical coupling and the level of optical coupling.

FIG. 6 illustrates a coordinate system for measuring device motion. In general, the device 600 may be a wrist worn device or any of the other devices described herein. A coordinate system for the device 600 may include an x axis 602 in a plane substantially parallel to the user's skin where it contacts the device 600 when placed for use, but substantially normal to a strap 604 retaining the device in position. While it is understood that the strap is a complex contoured surface, in this context, normal to the strap should be understood to mean substantially normal to a plane intersecting a path following a band of tension circumferentially around the strap, or stated alternatively, substantially normal to a long axis of the device (e.g., they axis 606 in FIG. 6) and substantially parallel to a short axis of the device (e.g., the x axis 602 in FIG. 6) as illustrated. The coordinate system may also include a y axis 606 substantially in the plane parallel to the user's skin and parallel to the strap 604, e.g., substantially parallel to the plane through the strap described above. The coordinate system may include a z axis 608 substantially perpendicular to a plane that is substantially parallel to the user's skin where it contacts the device 600 when placed for use. Accelerometers such as any of those described herein may be positioned to measure movement in each of the x axis 602, they axis 606, and the z axis 608, e.g., for measurement of mechanical or optical coupling as described herein. Gyroscopes such as any of those described herein may also or instead be positioned to measure rotation about each of the x axis 602, they axis 606, and the z axis 608, e.g., for measurement of mechanical or optical coupling as described herein.

Figure 7:
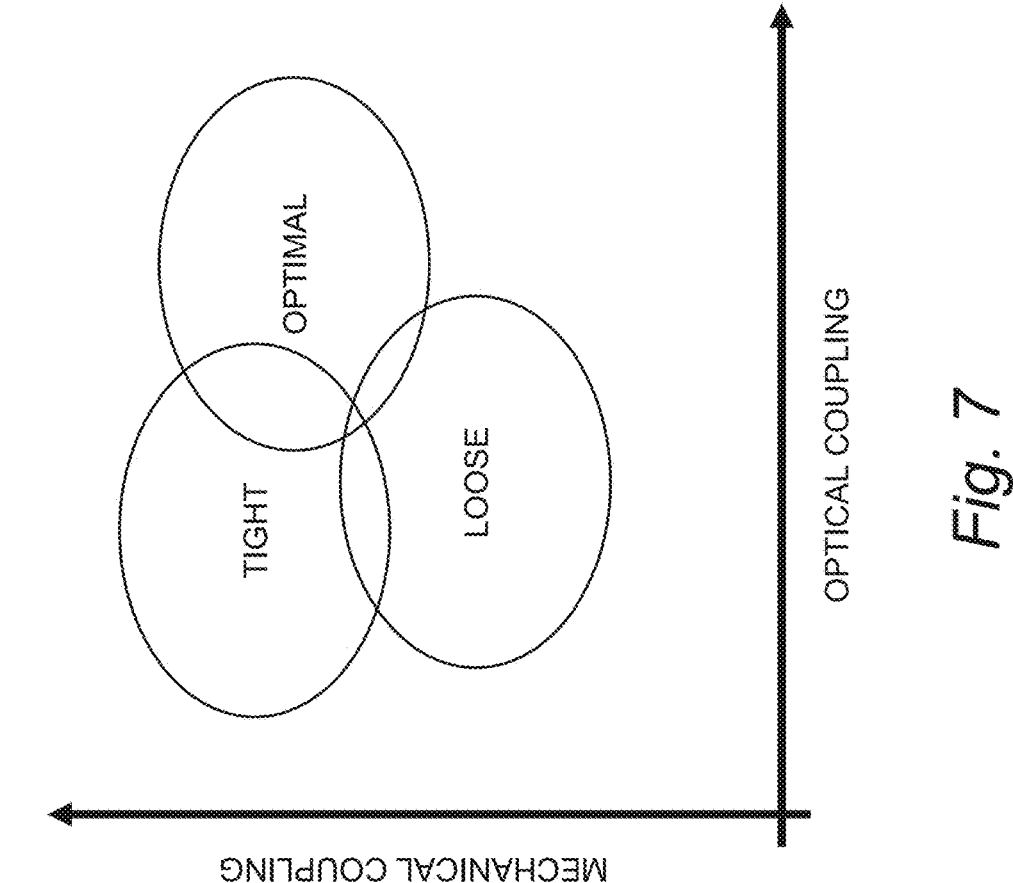
FIG. 7 illustrates a mapping of mechanical and optical coupling to device fit.

FIG. 7 illustrates a mapping of optical and mechanical coupling to device fit. In general, ranges of mechanical coupling and optical coupling, as described herein, may be mapped to categories of fit. It will be understood that the categories and locations are conceptual only, and that the contours of any particular category, and/or the ranges of corresponding measured mechanical or optical coupling, will depend on the particular type of device, the location of the device, and the particular type of restraint system. Thus, for example, the nature of mechanical coupling and/or optical coupling for a properly tensioned device in a pocket of a wearable garment may be significantly different than the nature of mechanical coupling and/or optical coupling for a properly tensioned device strapped to a wearer's wrist. However, in general, ranges of optical and mechanical coupling have been demonstrated as reliably correlated to proper or improper tension, and may be used to generate user recommendations for adjustments as contemplated herein.

Figure 8:
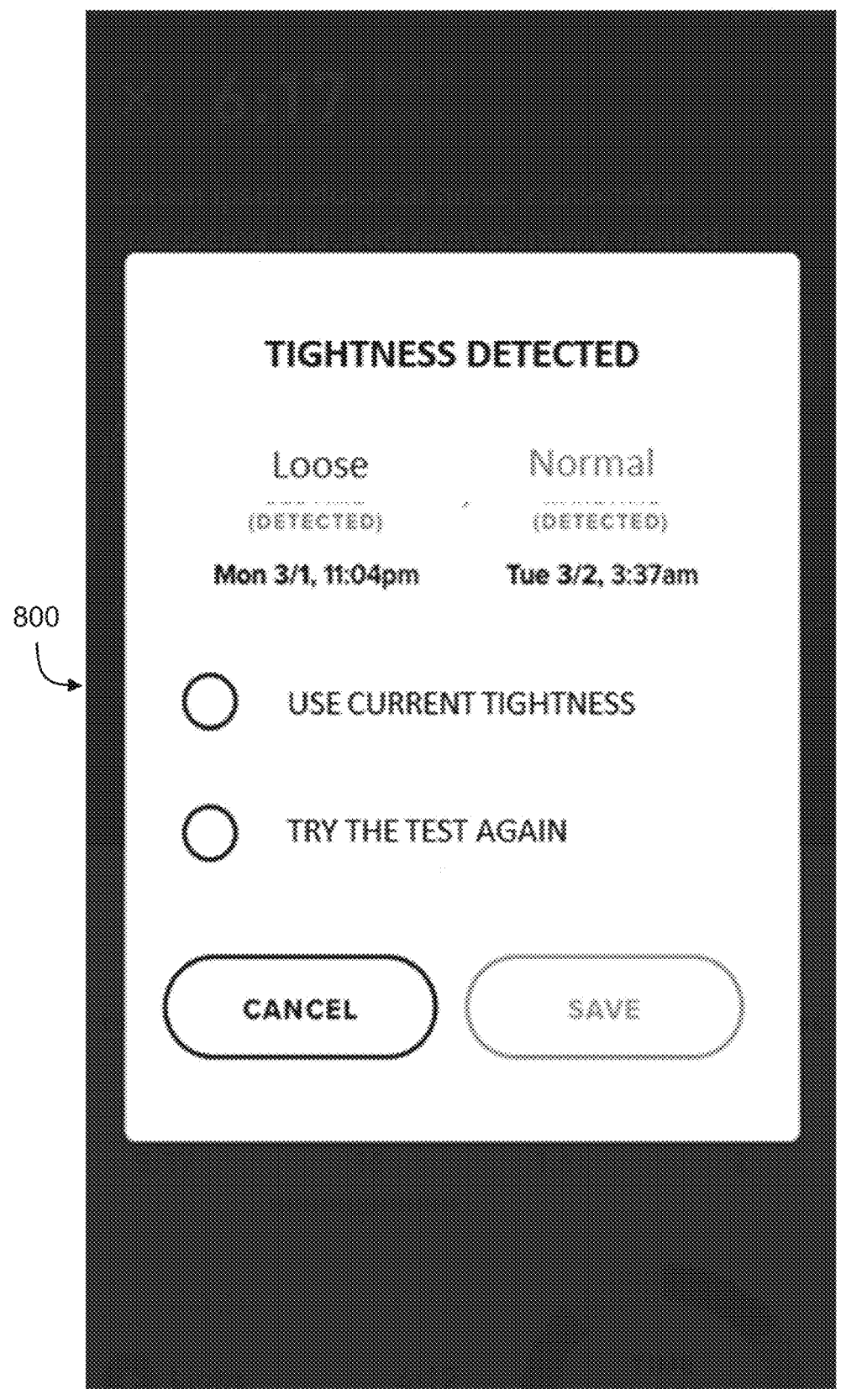
FIG. 8 illustrates a user interface for user interactions with a device fit protocol.

FIG. 8 shows a user interface 800 for user interactions with a device fit protocol, such as any of the user operations described herein. In general, the user interface 800 may be rendered in a smart phone application, web page, or other environment using any of the computing devices described herein. In general, the user interface 800 may be launched, e.g., in response to a user request for a test, in response to an event such as detecting that a user has started wearing a device, in response to a drop of data quality below a threshold, and/or on some predetermined schedule (e.g., once a day or once a week, upon waking, and the like). The user interface 800 may present user options, such as using a current tightness, or running a test again, e.g., after a user has made an adjustment based on device feedback. The user interface 800 may display, e.g., a quantitative and/or qualitative assessment of current fit, and/or a history of fit assessments for the user and device.

In another aspect, the selection of a model or parameters for analyzing fit may depend on where the device is located and/or the type of device (e.g., a device strapped to the body, a device in a garment pocket, an optical sensor, an electrical sensor, etc.). As such, a location detection algorithm may be used to determine a location of the wearable monitor on the body based on data from, e.g., accelerometers, gyroscopes, optical sensors, and other sensors integrated into the wearable monitor, in order to facilitate the selection of a suitable model for evaluating fit. This may be particularly useful where, e.g., the monitor might be deployed on a wrist band or at other body locations where it might be retained, e.g., with an athletic apparel garment such as a sock, shirt, pants, or the like, or some other elastic strap or combination of straps. The location of a monitor such as a photoplethys-mography-based heart rate monitor may imply different tension requirements, e.g., where the tension/location combination as a significant impact on the selection of algorithms or models to process data, e.g., to account for different motion cancelation needs at different locations, to support the identification of suitable heart rate calculation algorithms. The location may also more specifically affect the selection and use of different physical models for evaluating fit as described herein.

Figure 9:
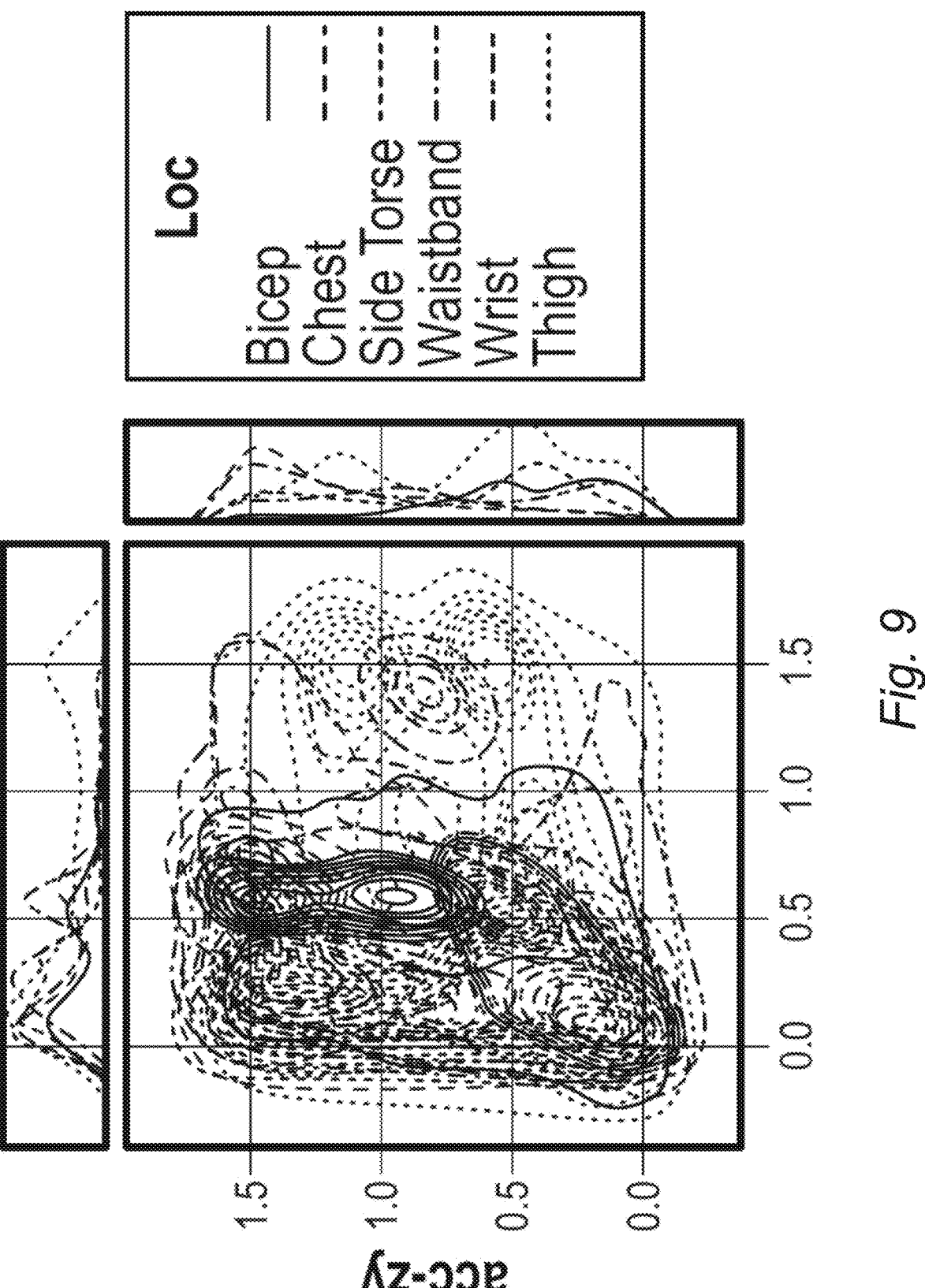
FIG. 9 shows motion data from a wearable monitor.

In one aspect, a data driven algorithm may be used to find a location of a wearable monitor without user input by using sensors such as motion sensors and touch sensors within the wearable monitor. In general, the physical orientation and motion of accelerometers and gyroscopes will depend on the location of a monitor on the body. For example, when the user moves forward, a monitor on the torso maintains a fix relation between two set of sensors while when the monitor is on the wrist this relationship changes continuously. FIG. 9 shows accelerometer data patterns for different regions of the body. These empirical patterns of accelerometer data may be used to estimate sensor location, e.g., by mapping motion data from the sensor to one or more regions of these patterns. Similar patterns may be used based on, e.g., magnitude, cross-correlation, rotation (e.g., gyroscopic measurements), and the like to identify sensor location, which may be used, in turn to select suitable data models for evaluating fit as described herein.

Figure 10:
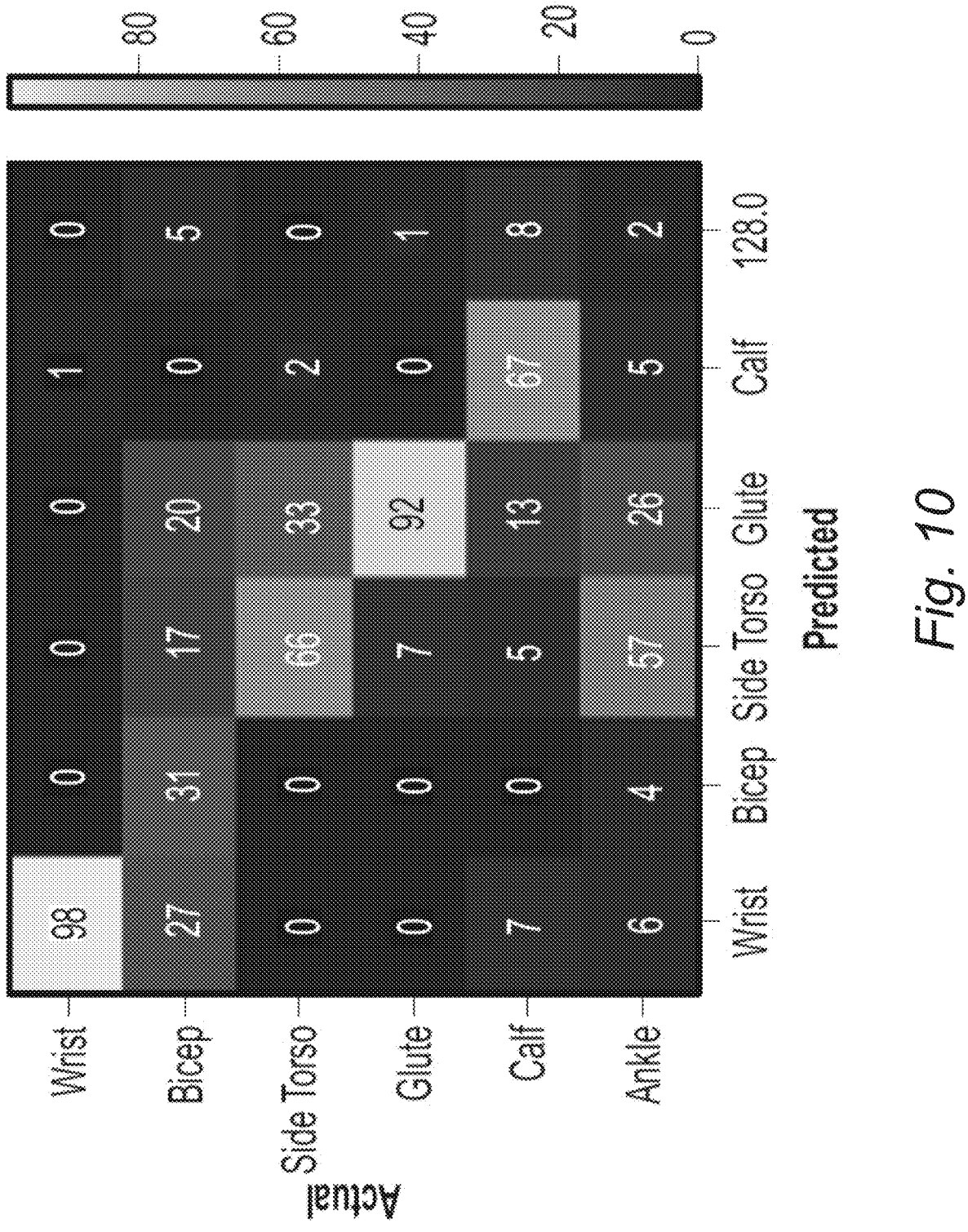
FIG. 10 shows a confusion matrix for data-driven predictions of body location for a wearable monitor.
Figure 11:
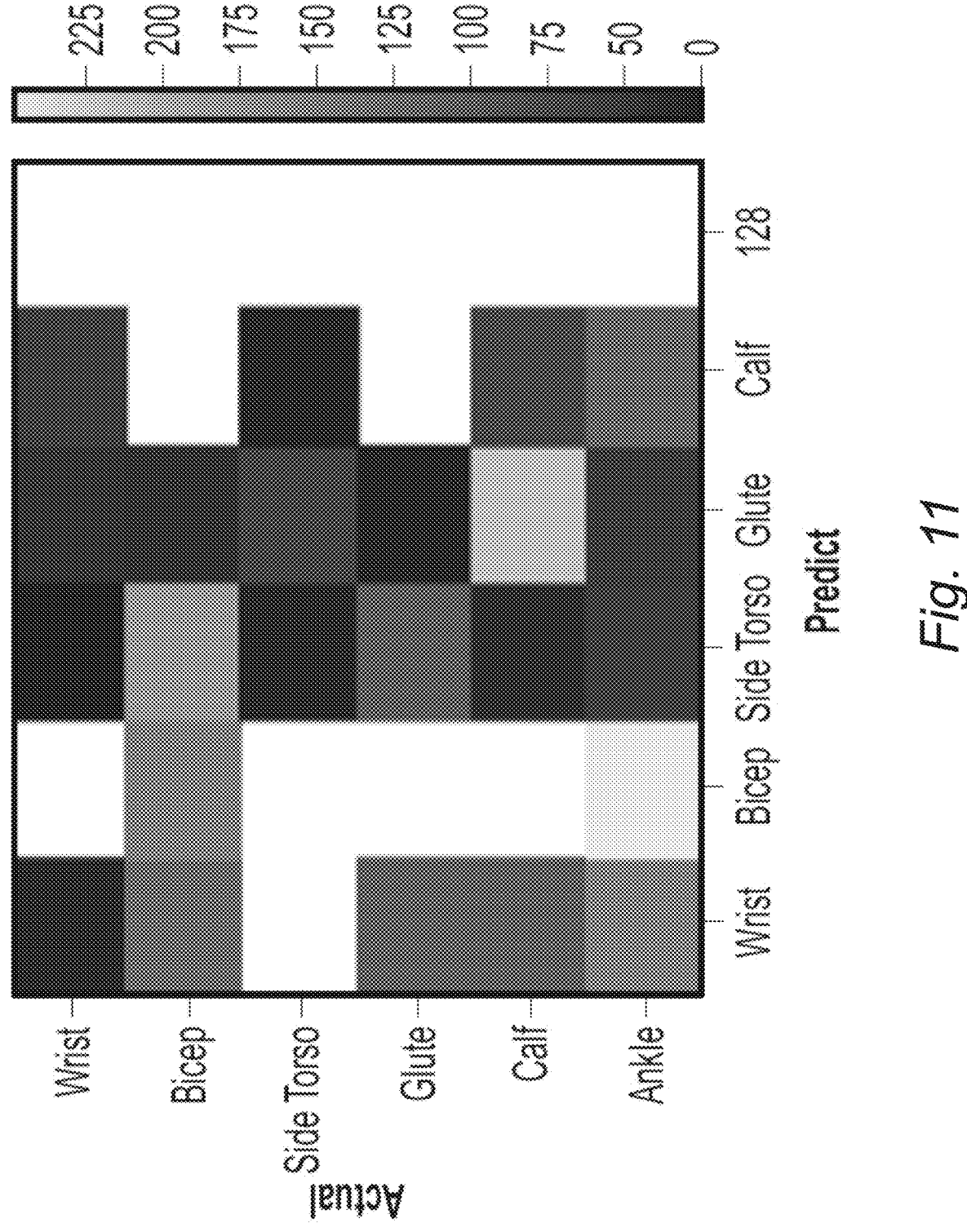
FIG. 11 illustrates the time to achieve a 95% confidence level in location predictions for a wearable monitor on a number of body locations.

For a range of users and a range of monitor locations, a data driven model may be used to detect location during rest, activities with harmonic motion, and activities with non-harmonic motion. FIG. 10 shows a confusion matrix comparing actual results to predicted results using the data driven model. FIG. 11 shows an amount of time (in seconds of activity) required to achieve a 95% confidence in location for each of the test locations using the techniques described above. In general, these figures illustrate that a data driven model can be derived to usefully detect object location based on sensor data from a wearable monitor over a range of body locations including at least a wrist, bicep, side torso, glute, calf, and ankle. This data may be used to select a resonance model corresponding to the object location for use in estimating strap tension (e.g., method 400 in FIG. 4), or more generally to select processing models, filters, parameters, and the like for processing data from a wearable monitor, particularly in contexts where the monitor is specifically adapted for use on a variety of body locations. For example, it may be determined that the wearable monitor is located on a wrist of the user. A wrist-based model may then be selected for estimating strap tension or otherwise evaluating sensor fit.

More generally, a variety of models are known in the art for determining a location of a device on a user's body, and any such technique may be used, either alone or in combination with the technique described above, to estimate the device location for purposes of choosing suitable models to evaluate fit of a device and/or providing feedback for user adjustments to same.

The above systems, devices, methods, processes, and the like may be realized in hardware, software, or any combination of these suitable for the control, data acquisition, and data processing described herein. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

Thus, in one aspect, each method described above, and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same. In another aspect, means for performing the steps associated with the processes described above may include any of the hardware and/or software described above. All such permutations and combinations are intended to fall within the scope of the present disclosure.

The method steps of the implementations described herein are intended to include any suitable method of causing such method steps to be performed, consistent with the patentability of the following claims, unless a different meaning is expressly provided or otherwise clear from the context. So, for example, performing the step of X includes any suitable method for causing another party such as a remote user, a remote processing resource (e.g., a server or cloud computer) or a machine to perform the step of X. Similarly, performing steps X, Y, and Z may include any method of directing or controlling any combination of such other individuals or resources to perform steps X, Y, and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims.

What is claimed is:

1. A computer program product comprising computer executable code embodied in a non-transitory computer readable medium that, when executing on one or more computing devices, performs the steps of:

causing a vibration of a wearable heart rate monitor coupled to a body of a user with an elastic strap by activating a haptic output element on the wearable heart rate monitor;

measuring a response of the wearable heart rate monitor to the vibration, wherein the response includes an optical response from one or more optical sensors and a mechanical response from one or more motion sensors;

calculating a level of optical coupling of the wearable heart rate monitor to the user with a first signal from the one or more optical sensors;

calculating a level of mechanical coupling of the wearable heart rate monitor to the user with a second signal from the one or more motion sensors;

calculating a tension of a strap of the wearable heart rate monitor about the body by applying a physical model for the wearable heart rate monitor and the elastic strap to a combination of the level of optical coupling and the level of mechanical coupling; and providing adjustment information to the user based on the tension indicating whether the tension is within an acceptable range.

2. The computer program product of claim 1, wherein the physical model is a resonance model.

3. A method comprising:

causing a vibration of a wearable monitor coupled to a body of a user;

measuring a response of the wearable monitor to the vibration, wherein the response includes an optical response from one or more optical sensors and a mechanical response from one or more motion sensors;

calculating a level of optical coupling of the wearable monitor to the user with a first signal from the one or more optical sensors;

calculating a level of mechanical coupling of the wearable monitor to the user with a second signal from the one or more motion sensors;

evaluating a fit of the wearable monitor to the body based on a combination of the level of optical coupling and the level of mechanical coupling; and providing adjustment information to the user to adjust the fit to a predetermined target.

4. The method of claim 3, wherein the predetermined target includes a tension in a band securing the wearable monitor to the user.

5. The method of claim 3, wherein the predetermined target includes a normal force of the wearable monitor against a skin of the user.

6. The method of claim 3, wherein causing the vibration includes activating a haptic output element coupled to the wearable monitor.

7. The method of claim 3, wherein evaluating the fit includes calculating the level of mechanical coupling and the level of optical coupling with a processor on the wearable monitor.

8. The method of claim 3, wherein providing the adjustment information to the user includes presenting the adjustment information in a user interface of a computing device associated with the user.

9. The method of claim 3, wherein the adjustment information indicates a level of tightness of the wearable monitor.

10. The method of claim 3, wherein the adjustment information includes an instruction for adjusting the wearable monitor about the body.

11. The method of claim 3, wherein measuring the response includes receiving motion data during the vibration from one or more accelerometers.

12. The method of claim 3, wherein measuring the response includes receiving motion data during the vibration from one or more gyroscopes.

13. The method of claim 3, wherein measuring the response includes receiving optical data during the vibration from one or more light detectors.

14. The method of claim 3, wherein causing the vibration includes activating a linear haptic output element.

15. The method of claim 3, wherein the wearable monitor is coupled to a wrist of the user with a wristband.

16. The method of claim 3, wherein the wearable monitor is coupled to the body with an elastic article of clothing.

17. A system comprising:

a wearable monitor including a processor, at least one sensor, and a haptic output element;

computer executable code stored in a memory of the wearable monitor that configures the processor to cause a vibration of the haptic output element and receive a response to the vibration from the at least one sensor, wherein the response includes an optical response from one or more optical sensors and a mechanical response from one or more motion sensors; and a remote processing resource coupled in a communicating relationship with the wearable monitor, the remote processing resource including a second memory storing a physical model of the wearable monitor and a second processor configured to receive the response to the vibration from the wearable monitor, to calculate a level of mechanical coupling of the wearable monitor about a body of a user based on the response, to calculate a level of optical coupling of the wearable monitor about the body independently from the level of mechanical coupling based on the response, to evaluate a fit of the wearable monitor to the user based on a combination of the level of optical coupling and the level of mechanical coupling, and to communicate adjustment information to the user based on a difference between the fit and a predetermined target fit for the wearable monitor.

18. The system of claim 17, wherein the predetermined target fit includes at least one of a minimum tension, a maximum tension, and a range of tensions.

19. The system of claim 17, wherein the predetermined target fit includes at least one of a minimum threshold, a maximum threshold, and a range.

20. The method of claim 3, wherein evaluating the fit includes evaluating the fit based on a location of the wearable monitor.

* * * * *